(12) United States Patent
Young et al.

(10) Patent No.: US 9,443,203 B2
(45) Date of Patent: Sep. 13, 2016

(54) AMBULATION PREDICTION CONTROLLER FOR LOWER LIMB ASSISTIVE DEVICE

(71) Applicant: REHABILITATION INSTITUTE OF CHICAGO, Chicago, IL (US)

(72) Inventors: Aaron Young, Chicago, IL (US); Levi Hargrove, Chicago, IL (US)

(73) Assignee: REHABILITATION INSTITUTE OF CHICAGO, Chicago, IL (US)

( * ) Notice: Subject to any disclaimer, the term of this patent is extended or adjusted under 35 U.S.C. 154(b) by 377 days.

(21) Appl. No.: 13/925,668

(22) Filed: Jun. 24, 2013

(65) Prior Publication Data

US 2015/0262076 A1    Sep. 17, 2015

(51) Int. Cl.
   G06N 99/00    (2010.01)
   A61F 2/60     (2006.01)
   A61F 2/70     (2006.01)
   G06F 17/30    (2006.01)

(52) U.S. Cl.
   CPC ............. *G06N 99/005* (2013.01); *A61F 2/60* (2013.01); *A61F 2/70* (2013.01); *G06F 17/30424* (2013.01); *A61F 2002/704* (2013.01)

(58) Field of Classification Search
   CPC ................................................... G06N 99/005
   See application file for complete search history.

(56) References Cited

U.S. PATENT DOCUMENTS

| | | | |
|---|---|---|---|
| 2011/0190593 A1* | 8/2011 | McNair | A61B 5/00 600/300 |
| 2011/0257764 A1 | 10/2011 | Herr et al. | |
| 2012/0083901 A1 | 4/2012 | Langlois et al. | |
| 2013/0060349 A1 | 3/2013 | Thorsteinsson et al. | |
| 2013/0218053 A1* | 8/2013 | Kaiser | A61B 5/1123 600/595 |

FOREIGN PATENT DOCUMENTS

| | | |
|---|---|---|
| WO | 2010/027968 A2 | 3/2010 |
| WO | 2011/083172 A1 | 7/2011 |

OTHER PUBLICATIONS

International Search Report and Written Opinion of the ISA/EP issued in related application PCT/US2014/043863, dated May 7, 2015, 15 pages.
Hargrove, L.J. et al., "A Comparison of Surface and Intramuscular Myoelectric Signal Classification", IEEE Transactions on Biomedical Engineering, May 2007, 54(5):847-853.
Au, S. K., et al., "Biomechanical Design of a Powered Ankle-Foot Prosthesis", Proceedings of the 2007 IEEE 10th International Conference on Rehabilitation Robotics, Jun. 12-15, 2007, pp. 298-303.
Au, S., et al., "Powered Ankle-foot Prosthesis Improves Walking Metabolic Energy", IEEE Transactions on Robotics, Feb. 2009, 25(1):51-66.

(Continued)

*Primary Examiner* — Alan Chen
(74) *Attorney, Agent, or Firm* — Drinker Biddle & Reath LLP

(57) ABSTRACT

Embodiments of the systems and methods described herein relate to a control unit comprising a memory having stored thereon a feature database that includes feature data, a portion of which is labeled with a transition from an ambulation mode and a memory having stored thereon a pattern recognition controller that is trained using the labeled feature data, wherein the pattern recognition controller is configured to predict the ambulation mode of an assistive device and the control unit is configured to communicate with sensors coupled to the assistive device.

73 Claims, 10 Drawing Sheets

(56) References Cited

OTHER PUBLICATIONS

Au, S., et al., "Powered ankle-foot prosthesis to assist level-ground and stair-descent gaits," Neural Netw, Apr. 26, 2008, 21:654-666.

Bellman, M., et al., "Immediate Effects of a New Microprocessor-Controlled Prosthetic Knee Joint: a Comparative Biomechanical Evaluation", Arch Phys Med Rehabil, Mar. 2012, 93:541-549.

Ceseracciu, E., et al., "SVM classification of locomotion modes using surface electromyography for applications in rehabilitation robotics", 19th IEEE International Symposium on Robot and Human Interactive Communication, Sep. 12-15, 2010, pp. 165-170.

Chan, A.D.C. et al., "Multiexpert Automatic Speech Recognition Using Acoustic and Myoelectric Signals," IEEE Transactions on Biomedical Engineering, Apr. 2006, 53(4):676-685.

Davies, B., et al., "Mobility outcome following unilateral lower limb amputation", Prosthetics and Orthotics International, 2003, 27:186-190.

Dillingham, T.R., et al., "Limb Amputation and Limb Deficiency: Epidemiology and Recent Trends in the United States," Southern Medical Journal, Aug. 2002, 95(8):875-883.

Farrell, M. T., et al., "A method to determine the optimal features for control of a powered lower-limb prostheses", 33rd Annual International Conference of the IEEE EMBS, Aug. 30-Sep. 3, 2011, pp. 6041-6046.

Fite, K., et. al, "Design and Control of an Electrically Powered Knee Prosthesis", Proceedings of the 2007 IEEE10th IEEE International Conference on Rehabilitation Robotics, 2007, pp. 902-905.

Flowers, W.C., et al., "Electrohydraulic knee-torque controller for a prosthesis simulator", ASME Journal of Biomechanical Engineering, Jun. 12-15, 1977, 99:3-8.

Gales, M., et al., "The Application of Hidden Markov Models in Speech Recognition", Foundations and Trends in Signal Processing, 2007, 1(3):195-304.

Hafner, B.J., et al., "Evaluation of Function, Performance, and Preference as Transfemoral Amputees Transition From Mechanical to Microprocessor Control of the Prosthetic Knee," Archives of Physical Medicine and Rehabilitation, Feb. 2007, 88:207-217.

Hargrove, L.J., et al., "Real-Time Myoelectric Control of Knee and Ankle Motions for Transfemoral Amputees", JAMA, Apr. 20, 2011, 305(15):1542-1544.

Highsmith, M.J., et al., "Kinetic Differences Using a Power Knee and C-Leg While Sitting Down and Standing Up: A Case Report," Journal of Prosthetics & Orthotics, 2010, 22(4):237-243.

Hitt, J.K., et al., "An Active Foot-Ankle Prosthesis With Biomechanical Energy Regeneration," Journal of Medical Devices, Mar. 2010, 4:011003 1-9.

Holgate, M.A., et al., "The SPARKy (Spring Ankle with Regenerative Kinetics) Project: Choosing a DC Motor Based Actuation Method," Proceedings of the 2nd Biennial IEEE/RAS-EMBS International Conference on Biomedical Robotics and Biomechatronics, Oct. 19-22, 2008, pp. 163-168.

Huang, H., et al., "A Strategy for Identifying Locomotion Modes using Surface Electromyography," IEEE Transactions on Biomedical Engineering, Jan. 2009, 56:65-73.

Huang, H., et al., "Continuous Locomotion-Mode Identification for Prosthetic Legs Based on Neuromuscular Mechanical Fusion," IEEE Transactions on Biomedical Engineering, Oct. 2011, 58(10):2867-2875.

Hudgins, B., et al., "A New Strategy for Multifunction Myoelectric Control," IEEE Transactions on Biomedical Engineering, Jan. 1993, 40(1):82-94.

Kim, P.S., et al., "The Effects of Targeted Muscle Reinnervation on Neuromas in Rabbit Rectus Abdominis Flap Model", J Hand Surg Am, 2012, 37:1609-1616.

Kuiken, T.A., et al., "Targeted Muscle Reinnervation for Real-Time Myoelectric Control of Multifunction Artificial Arms," JAMA, Feb. 11, 2009, 301(6):619-628.

Lawson, B.E., et al., "Standing Stability Enhancement With an Intelligent Powered Transfemoral Prosthesis," IEEE Transactions on Biomedical Engineering, Sep. 2011, 58(9):2617-2624.

Lawson, B.E., et al., "Control of Stair Ascent and Descent with a Powered Transfemoral Prosthesis," IEEE Trans Neural Syst Rehabil Eng, May 2013, 21(3):466-473.

Li, G., et al., "Quantifying Pattern Recognition-Based Myoelectric Control of Multifunctional Transradial Prostheses," IEEE Transactions on Neural Systems and Rehabilitation Engineering, Apr. 2010, 18(2):185-192.

Lock, B.A., et al., "Prosthesis-Guided Training for Practical Use of Pattern Recognition Control of Prostheses," from "MEC 11 Raising the Standard," Proceedings of the 2011 MyoElectric Controls/Powered Prosthetics Symposium, Aug. 14-19, 2011, 4 pages.

Martinez-Villalpando, E.C., et al., "Design of an Agonist-Antagonist Active Knee Prosthesis," Proceedings of the 2nd Biennial IEEE/RAS-EMBS International Conference on Biomedical Robotics and Biomechatronics, Oct. 19-22, 2008, pp. 529-534.

Miller, W.C., et al., "The Prevalence and Risk Factors of Falling and Fear of Falling Among Lower Extremity Amputees," Archives of Physical Medicine and Rehabilitation, Aug. 2001, 82:1031-1037.

Nefian, A.V., et al., "Dynamics Bayesian Networks for Audio-Visual Speech Recognition," EURASIP Journal on Applied Signal Processing, 2002, 11:1274-1288.

Parker, P., et al., "Myoelectric signal processing for control of powered limb prostheses," Journal of Electromyography and Kinesiology, Dec. 2006, 16:541-548.

Rabiner, L.R., "A Tutorial on Hidden Markov Models and Selected Applications in Speech Recognition," Proceedings of the IEEE, Feb. 1989, 77(2):257-286.

Schmalz, T., et al., "Biomechanical analysis of stair ambulation in lower limb amputees," Gait & Posture, 2007, 25:267-278.

Segal, A.D., et al., "Kinematic and kinetic comparisons of transfemoral amputee gait using C-Leg and Mauch SNS prosthetic knees," Journal of Rehabilitation Research & Development, Nov./Dec. 2006, 43(7):857-870.

Sensinger, J.W., et al., "Adaptive Pattern Recognition of Myoelectric Signals: Exploration of Conceptual Framework and Practical Algorithms," IEEE Transactions on Neural Systems and Rehabilitation Engineering, Jun. 2009, 17:270-278.

Song, L., et al., "Time-Varying Dynamic Bayesian Networks", Computer, 2009, 22:1-9.

Sup, F., et al., "Design and Control of a Powered Knee and Ankle Prosthesis," 2007 IEEE International Conference on Robotics and Automation, Apr. 10-14, 2007, pp. 4134-4139.

Sup, F., et al., "Design and Control of a Powered Transfemoral Prosthesis," The International Journal of Robotics Research, Feb. 2008, 27(2):263-273.

Sup, F., et al., "Preliminary Evaluations of a Self-Contained Antrhopomorphic Transfemoral Prosthesis," IEEE/ASME Transactions on Mechatronics, Dec. 2009, 14(6):667-676.

Sup, F., et al., "Upslope Walking with a Powered Knee and Ankle Prosthesis: Initial Results with an Amputee Subject," IEEE Transactions on Neural Systems and Rehabilitation Engineering, Feb. 2011, 19(1):71-78.

Varol, H.A., et al., "Multiclass Real-Time Intent Recognition of a Powered Lower Limb Prosthesis", IEEE Transactions on Biomedical Engineering, Mar. 2010, 57(3):542-551.

Wang, N., et al., "Accelerometry Based Classification of Gait Patterns Using Empirical Mode Decomposition," IEEE International Conference on Acoustics, Speech and Signal Processing, 2008, pp. 617-620.

Waters, R.L., et al., "Energy cost of walking of amputees: the influence of level of amputation," Journal of Bone & Joint Surgery, 1976, 58:42-46.

Young, A.J., et al., "The Effects of Electrode Size and Orientation on the Sensitivity of Myoelectric Pattern Recognition Systems to Electrode Shift," IEEE Transactions on Biomedical Engineering, Sep. 2011, 58(9):2537-2544.

Young, A.J., et al., "Improving Myoelectric Pattern Recognition Robustness to Electrode Shift by Changing Interelectrode Distance and Electrode Configuration," IEEE Transactions on Biomedical Engineering, Mar. 2012, 59(3):645-652.

Zhou, P., et al., "Decoding a New Neural-Machine Interface for Control of Artificial Limbs", J Neurophysiol, 2007, 98:2974-2982.

Sup, F., et al., "Design and Control of an Active Electrical Knee and Ankle Prosthesis," Proc IEEE RAS EMBS Int Conf Biomed Robot Biomechatron, Oct. 19, 2008, pp. 523-528.

\* cited by examiner

AMBULATION PREDICTION CONTROLLER FOR LOWER LIMB ASSISTIVE DEVICE

This invention was made with government support under W81XWH-09-2-0020 awarded by the United States Army. The government has certain rights in the invention.

TECHNICAL FIELD

The disclosure refers generally to the field of human machine interfaces and specifically to intent recognition for the control of lower-limb assistive devices.

BACKGROUND

Transfemoral (i.e. above-knee) amputation is a significant cause of disability in the United States with approximately 31,000 new cases occurring each year. Transfemoral amputees may use an assistive device known as an artificial leg, or a prosthesis, to replace a missing natural leg.

Transfemoral prostheses have traditionally been mechanically passive devices, which are controlled by mechanical interaction with the subject's limb. A passive prosthesis uses springs, dampers, or other passive devices that do not provide external energy to power the prosthesis. Passive lower-limb prostheses provide a lower limb amputee or other user with a limited range of ambulation modes, such as standing, walking, ascending or descending ramps, or climbing up and down stairs. Transfemoral amputees who use passive prostheses have significantly impaired balance, walking symmetry, and metabolic energy efficiency. They also tend to have difficulty navigating more demanding terrain such as ramps or stairs. The use of an active transfemoral prosthesis, with the ability to generate positive mechanical power, greatly increases the number and nature of ambulation modes that can be restored to amputees.

Lower limb prosthesis users may desire to ambulate in several modes, including level walking, climbing stairs, descending stairs, climbing ramps, or descending ramps. Operation in multiple modes requires the prosthesis to be able to transition from one mode to another. The failure of a prosthesis to transition prevents the user from moving appropriately and can result in harm to the user. For instance, if a lower limb prosthesis user wishes to transition from walking to climbing stairs, the prosthesis must be raised so that its foot raises above the first step. Failure of the prosthesis to transition appropriately can result in the device hitting the stairs, potentially damaging the prosthesis and causing injury to the user through a fall or other event.

DETAILED DESCRIPTION

Various embodiments of the systems and methods described herein relate to an improved ambulation controller for predicting the ambulation mode of an assistive device, such as a lower limb prosthetic or orthotic.

Various embodiments of the systems and methods described herein relate to an improved method of training an ambulation controller in order to predict the ambulation mode of an assistive device.

Various embodiments of the systems and methods described herein relate to an assistive device that provides automatic transitions between ambulation modes. An assistive device provides automatic transitions between ambulation modes if a button or other actuator does not need to be pressed to transition the assistive device from one ambulation mode to another.

Various embodiments of the systems and methods described herein relate to an assistive device that provides seamless transitions between ambulation modes. An assistive device provides seamless transitions between ambulation modes if the user does not have to stop or is not perturbed (i.e. the assistive device kicks or otherwise disrupts the user's gait while in use) when the assistive device transitions from one ambulation mode to another.

Various embodiments of the systems and methods described herein relate to an assistive device that provides natural transitions between ambulation modes. An assistive device provides natural transitions between ambulation modes if the user does not need to perform additional movement, such as shaking the assistive device of providing additional muscle contraction in order to transition the assistive device from one ambulation mode to another.

Figure 1:
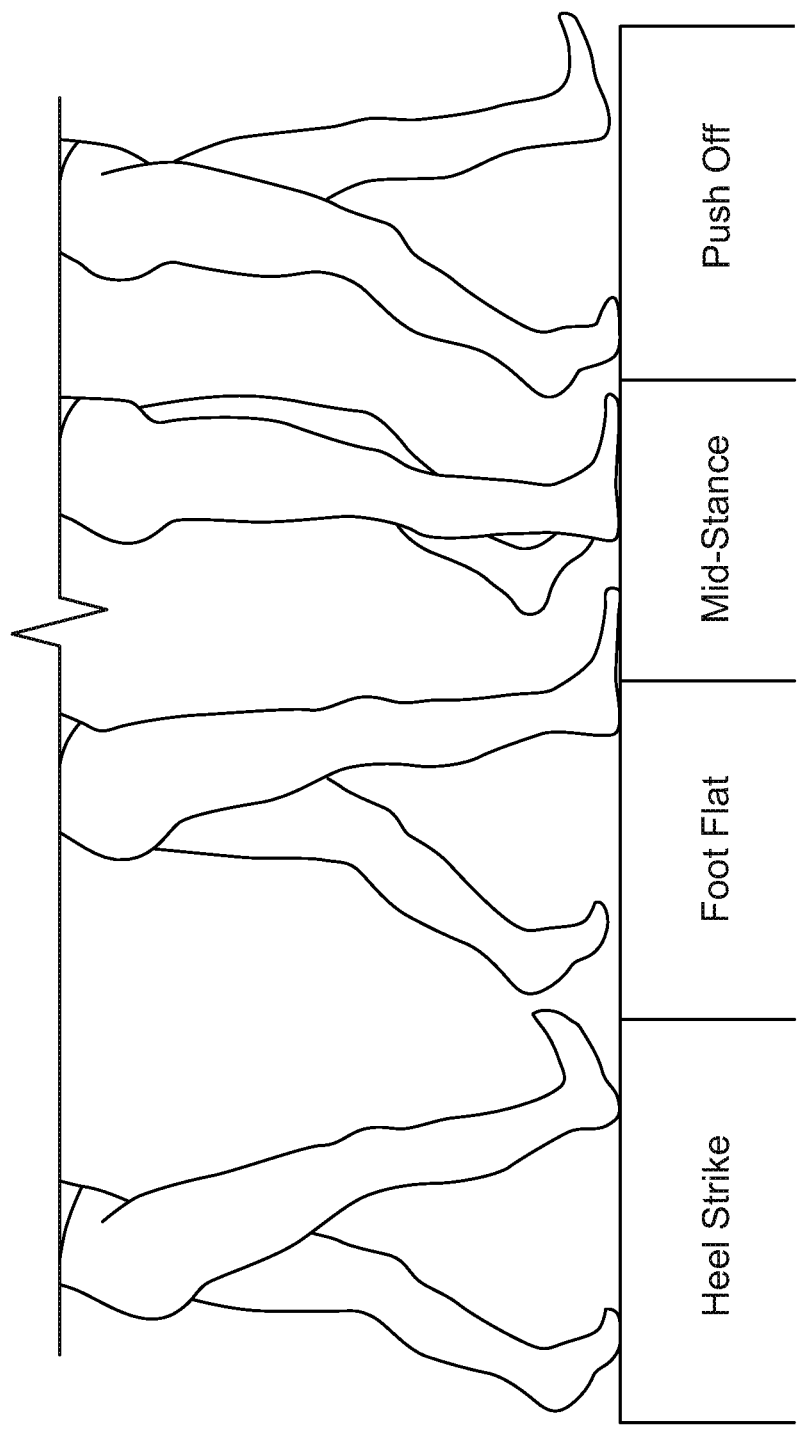
FIG. 1 depicts different gait phases of a stride.

A general description of gait cycle and gait phase will now be provided. A gait cycle is the period of motion between a complete cycle of a gait. As an example, a gait cycle starts when the heel of one foot touches the ground, continues through the toe-off and swing phases of the leg, and finishes when the heel of the same foot again touches the ground. Completion of a single gait cycle by a user is called a stride. A gait phase is a segment of a gait cycle of a limb; for instance, stance phase (wherein the foot of the limb is touching the ground) and swing phase (wherein the foot of the limb is not touching the ground) are each gait phases. FIG. 1 shows the stance phase of a leg, which starts when the heel of the foot strikes the ground (herein known as "heel strike") and continues until the toe of the foot leaves the ground (herein known as "toe-off" or "push off").

Figure 2A:
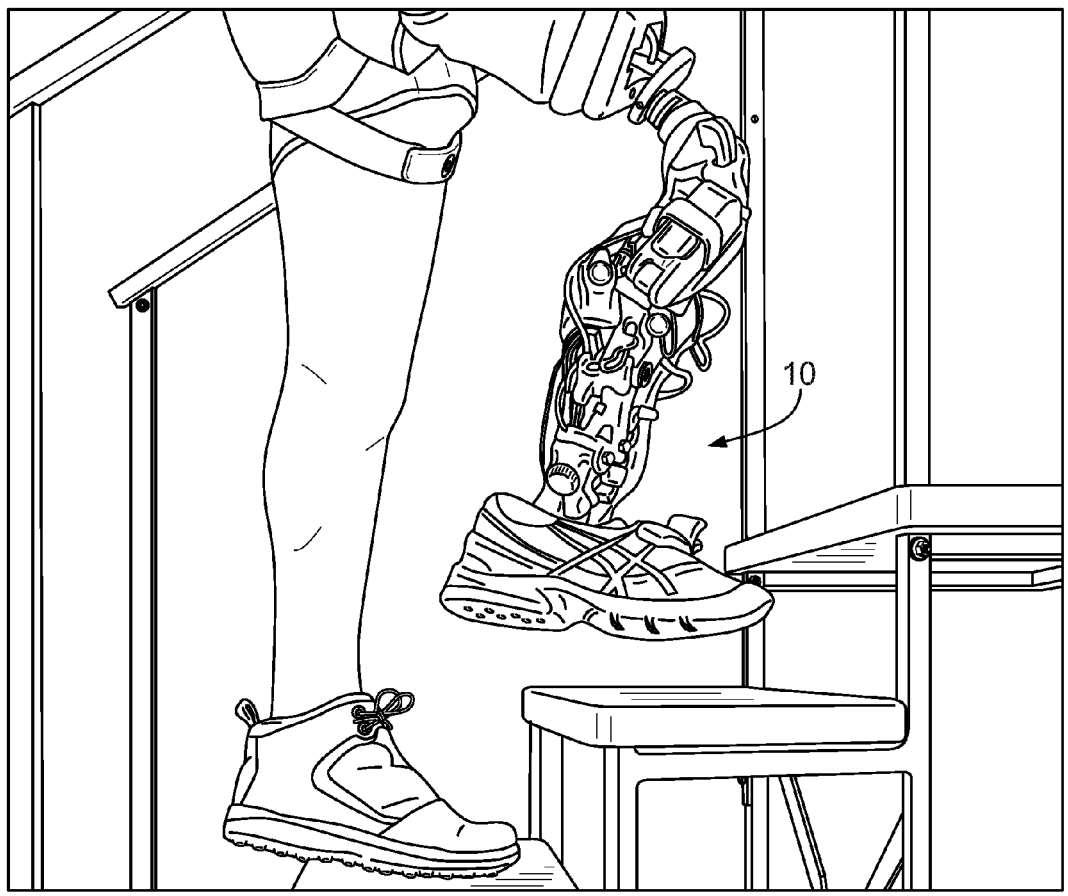
FIGS. 2a and 2b depict a possible implementation of assistive device 10.
Figure 2B:
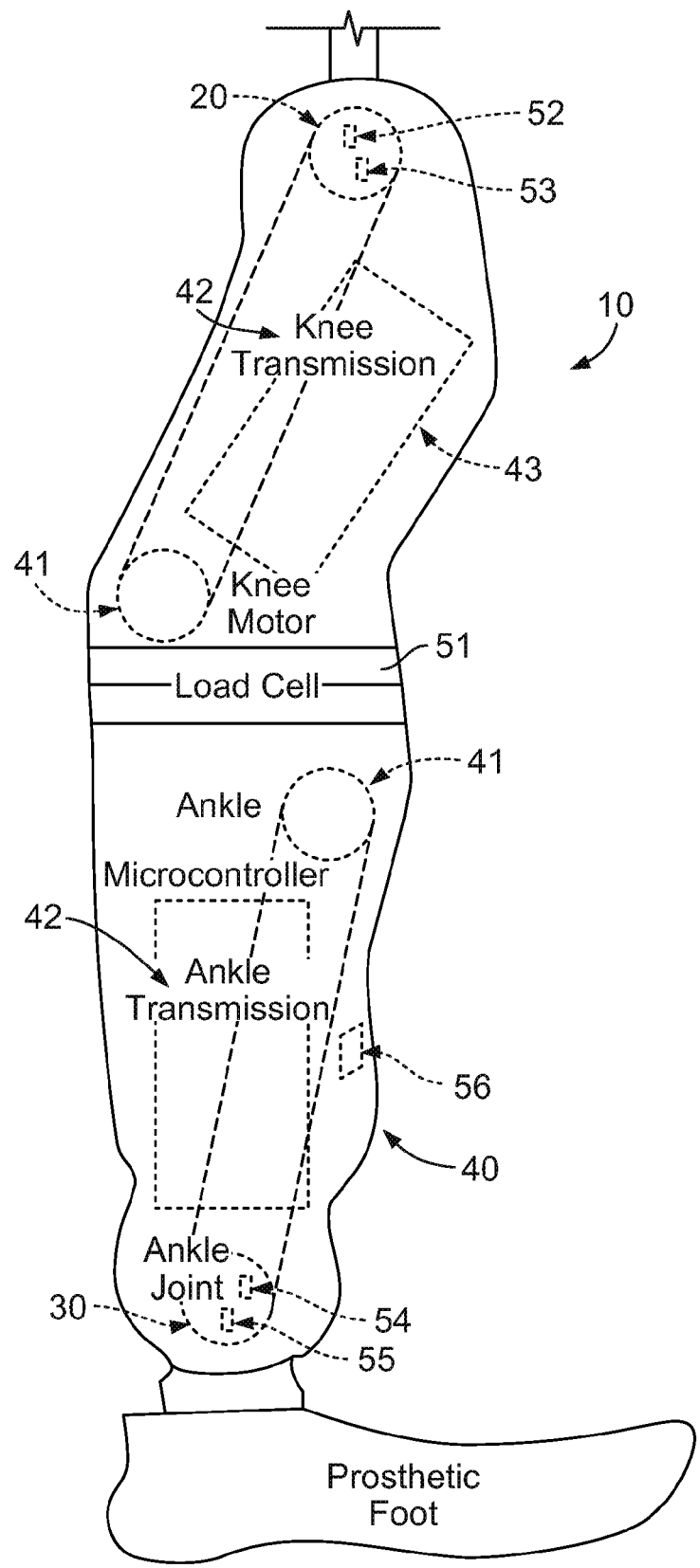

A detailed description of embodiments of the invention is provided with reference to the figures. FIGS. 2a and 2b depict assistive device 10. Assistive device 10 comprises powered knee 20, ankle 30, and shank 40. Knee 20 and ankle 30 are each coupled to one or more motors 41 and one or more transmissions 42 that together are capable of producing physiological levels of torque. Assistive device 10 and its related powered components are powered by battery 43.

Assistive device 10 further comprises mechanical sensors 50. In one embodiment, mechanical sensors 50 include load cell 51 that measures the vertical load along the long axis of assistive device 10; position sensor 52 and velocity sensor 53 that measure the position and velocity of the knee 20; position sensor 54 and velocity sensor 55 that measure the position and velocity of ankle 30; and a six degree of freedom inertial measurement unit 56 at shank 40, comprising accelerometers and gyroscopes for measuring accelerations and angular velocities. Mechanical sensors 50 may be contained within the assembly of assistive device 10, attached to assistive device 10, or attached to the user of assistive device 10. In other embodiments, knee 20 and ankle 30 could be powered instead with hydraulics, compressed gas, or other mechanisms.

Figure 3:
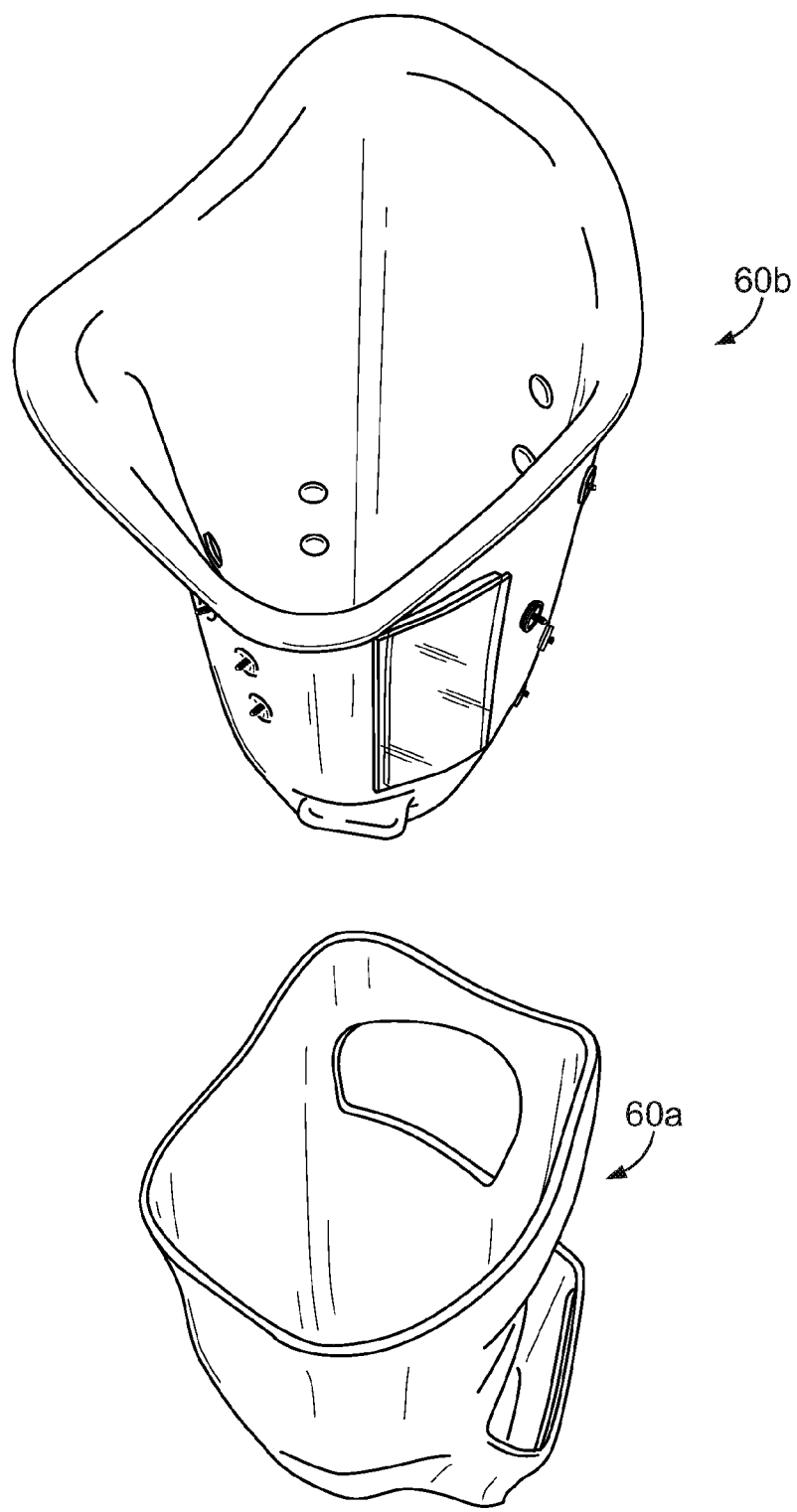
FIG. 3 depicts a socket to which the assistive device of FIGS. 2a and 2b may be coupled.

FIG. 3 displays a socket 60, into which fits the residual limb of a user. Socket 60 comprises lining 60a and exterior shell 60b. Assistive device 10 is coupled to socket 60 by a pyramid style connector or other appropriate connector. Socket 60 is coupled to electrodes 70. In one embodiment, electrodes 70 are embedded in socket 60 and contact the user's skin. Electrodes 70 measure EMG signals from the user's residual limb muscles when the user operates assistive device 10. In one embodiment, electrodes 70 may be placed on the following muscles of the user: semitendinosus, biceps femoris, tensor fasciae latae, rectus femoris, vastus lateralis, vastus medialis, sartorius, adductor magnus, and gracilis.

Figure 4:
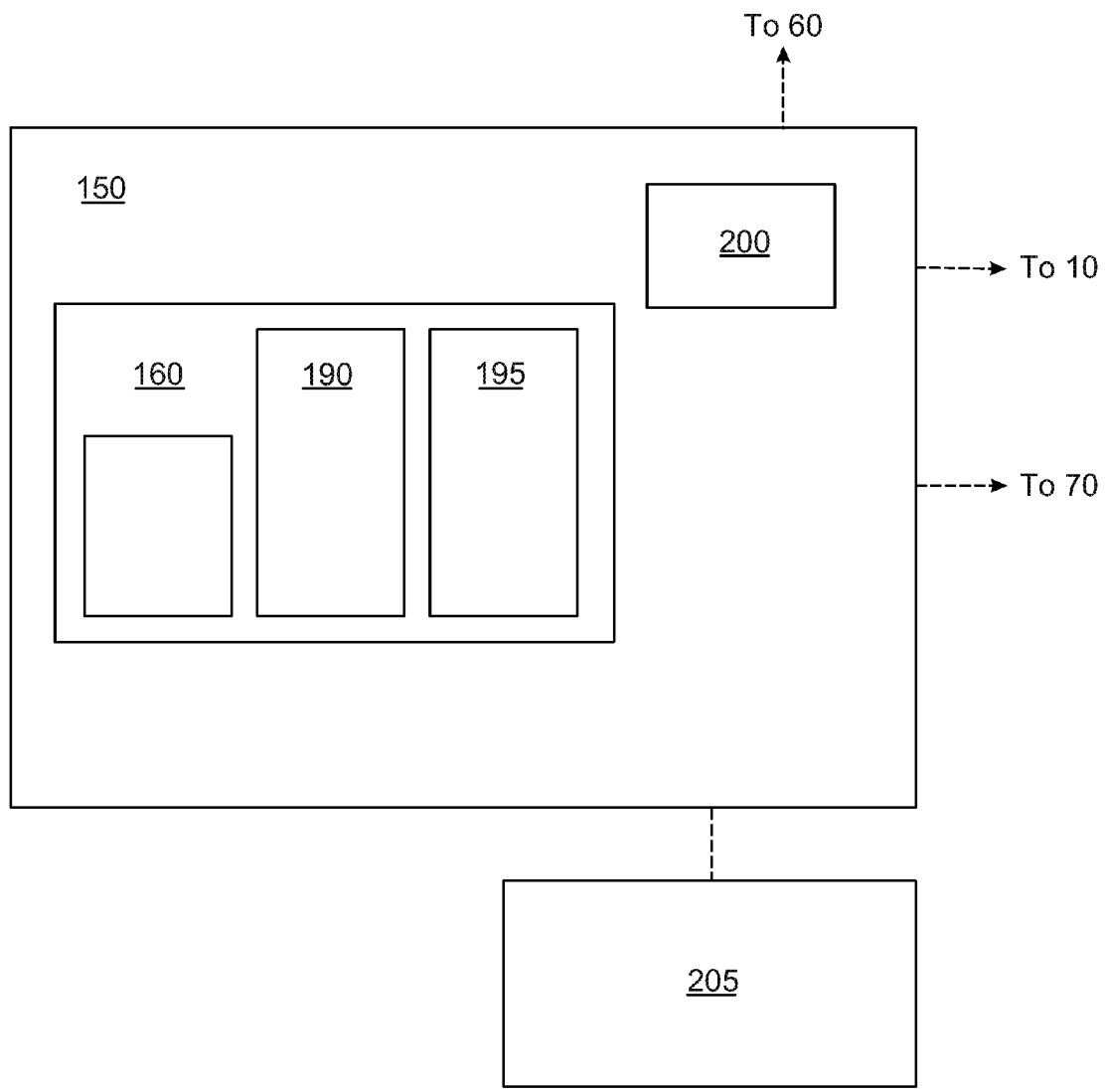
FIG. 4 is a diagram showing a possible implementation of the controller board 150.

FIG. 4 displays a representation of controller board 150. Controller board 150 is one embodiment of a control unit used to control assistive device 10. In one embodiment, controller board 150 is physically attached to socket 60 and connected to the components of assistive device 10 and to electrodes 70 by communication bus 160. Controller board 150 may comprise an off-the-shelf component, such as the Overo® Air Computer-On-Module (GUM3503A) (GumStix) or a custom built component. Controller board 150 comprises microprocessor module 160, such as the Texas Instruments OMAP 3503 Applications Processor with processor speed of 600 MHz, or another appropriate microprocessor. Microprocessor module 160 comprises non-volatile memory module 190 and RAM memory module 195. Signals from electrodes 70 are bandpass filtered in hardware between 20 Hz and 420 Hz and digitally sampled at 1000 Hz. Signals from mechanical sensors 50 are sampled at 500 Hz and the signals from load cell 51 are low pass filtered at 20 Hz.

Controller board 150 further comprises transceiver module 200 for communication with other components, such as computer unit 250 and training remote 300 (described below). In one embodiment, transceiver module 200 may be a wireless transceiver that is compatible with 802.11, Bluetooth, FM radio, or another wireless standard. Controller board 150 and its components may be powered from main battery 43 or by external power source 205, which provides power conditioning separate from main battery 43 and may comprise 12V or 20V lithium polymer battery. The details of the components on controller board 150 are exemplary and other components could be used.

Controller board 150 communicates via transceiver module 200 with computer unit 250. Computer unit 250 comprises a display, an input device (such as a keyboard, mouse, and/or touchpanel), a wireless module, a hard drive, a processor, an operating system, memory, and other known aspects of a computer system. Embodiments of computer unit 250 include, but are not limited to, a desktop computer system, a laptop computer system, a smartphone system, a tablet computer system, and other similar computer systems known in the art. Computer unit 250 is installed with control software 270 that provides a graphical user interface (GUI) 271. GUI 271 allows a user to communicate with controller board 150 in order to control and receive information from assistive device 10.

Figure 5:
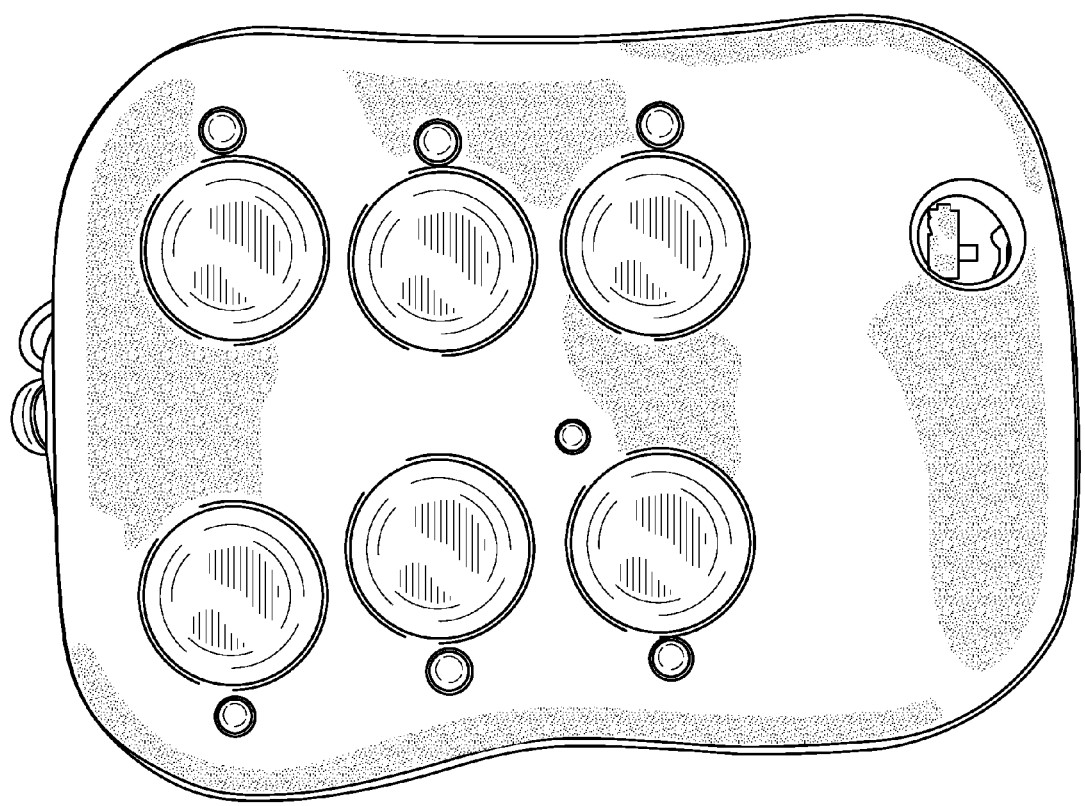
FIG. 5 depicts a possible implementation of training remote 300.

Training remote 300 comprises a wireless transceiver for communication with controller board 150. As shown in FIG. 5, in one embodiment, training remote 300 comprises a keyfob with multiple buttons. Each button on training remote 300 corresponds to a possible ambulation mode of assistive device 10. When a clinician (or other individual) presses a button on training remote 300, training remote 300 sends a signal to controller board 150 that causes assistive device 10 to change to the ambulation mode corresponding to the pressed button. Additional buttons on training remote 300 may be used to power on or off the motors of assistive device 10 or to update AMP 425 with new data. The capabilities of training remote 300 may be incorporated into computer unit 250, in another embodiment.

In one embodiment, microprocessor module 170 is programmed with an ambulation controller 400. Ambulation controller 400 comprises ambulation mode predictor (AMP) 425, phase state controller 450, and torque controller 475. Ambulation controller 400 is programmed in the C language and runs on a Linux operating system installed on microprocessor 160. Ambulation controller 400 may be loaded onto microprocessor module 160 wirelessly, by USB connection, or by other appropriate means.

An overview of the operation of certain embodiments described herein is now provided. AMP 425 is a pattern recognition controller and utilizes pattern recognition methods to predict the ambulation mode of assistive device 10. AMP 425 is trained using test data that may originate from a generalized training phase. AMP 425 may be further trained using level walking training data from a new user who did not participate in the generalized training phase. After AMP 425 has been trained, it may be used to predict the ambulation mode of a user operating assistive device 10 to walk, climb stairs, or perform other ambulations. At each heel strike and toe off of assistive device 10, ambulation controller 400 uses AMP 425 to predict the ambulation mode of the next stride of the user. AMP 425 may use one or more of the methods described herein to predict the ambulation mode of the next stride. Phase state controller 450 uses the mode predicted by AMP 425 to determine appropriate impedance values for assistive device 10. Torque controller 475 utilizes the phase state and impedance values from phase state controller 450 to cause motors 41 to operate assistive device 10 in the predicted ambulation mode, so that in the user's next stride, assistive device 10 operates in the predicted mode. Transition between ambulation modes at heel strike and toe off results in operation of assistive device 10 that is similar to operation of a natural leg, as the impedance parameter values of a natural leg also change at these state points. Additionally, transitioning ambulation modes at the heel contact and toe off prevents mode transition from occurring while the user has weight on assistive device 10 or while assistive device 10 is swinging.

Generalized training phase. AMP 425 utilizes a stored set of features to predict an ambulation mode. In one embodiment, AMP 425 utilizes a feature database 185 comprised of feature databases instantaneous feature database (IFD) 185i and stride feature database (SFD) 185s. Feature information for IFD 185i and SFD 185s may be generated during a generalized training phase.

Feature database 185 is stored on microprocessor module 160. Feature database 185 contains features 415 derived during use of assistive device 10 by multiple users over time. The number of users required to participate in the generalized training phase varies, although approximately ten or more users are preferred to ensure feature database 185 allows AMP 425 to accurately predict the next ambulation mode of assistive device 10 when it is being operated by a user. Users participating in the generalized training phase may have varying physical characteristics (including different heights, weights, and residual limb lengths) so that feature database 185 can contain a range of feature data.

In one embodiment of the generalized training phase, multiple users operate the assistive device 10 in various ambulation modes and in transitions between ambulation modes. First, a clinician (such as a certified prosthetist) may align and attach assistive device 10 to socket 60. In one embodiment, a clinician then sets assistive device 10 to "level walk" mode through controller board 150. The user then spends approximately 20 minutes performing level walking using assistive device 10, while the clinician visually supervises the user to ensure the user is performing level walking Level walking tasks include short steps, long steps, turning, shifting from side to side. The user may walk in a line or in other directions. The clinician then sets assistive device 10 to another mode such as "ramp ascent," and the user repeats a procedure similar to the one involving level walking. Other modes are repeated similarly, with the clinician setting assistive device 10 to that mode and the user operating assistive device 10 in that mode. Collected data is labeled with the mode in which assistive device 10 operated while the data was being generated by mechanical sensors 50 and electrodes 70.

The user continues to operate assistive device 10 by performing transitions from one ambulation mode to another. Each user may complete 20 or more repetitions of a full locomotion circuit. The locomotion circuit involved the following locomotion modes and occurred sequentially with seamless transitions from mode to mode: standing→ level walking→ ramp ascent→ level walking→ turn around→ level walking→ ramp descent→ level walking→ turn→ level walking→ stair ascent→ level walking→ turn around→ level walking→ stair descent→ level walking→ turn and stop. The ramp was set at a 10 degree angle and a staircase consisting of four stairs was used for stair ascent/descent. It should be understood that alternate transition sequences may be performed by users during the generalized training phase and steeper or shallower ramp angles could be accommodated.

When a user transitions from one ambulation mode to another, at heel strike or toe off, the next ambulation mode of assistive device 10 is manually triggered by the clinician using training remote 300. During the transition, the clinician watches the user and presses a button on the training remote 300 when the user transitions from one ambulation mode to another. Training remote 300 transmits data to controller board 150 reflecting the next ambulation mode in which the user is operating. In this way, collected data is labeled with transitions from an ambulation mode.

Figure 6:
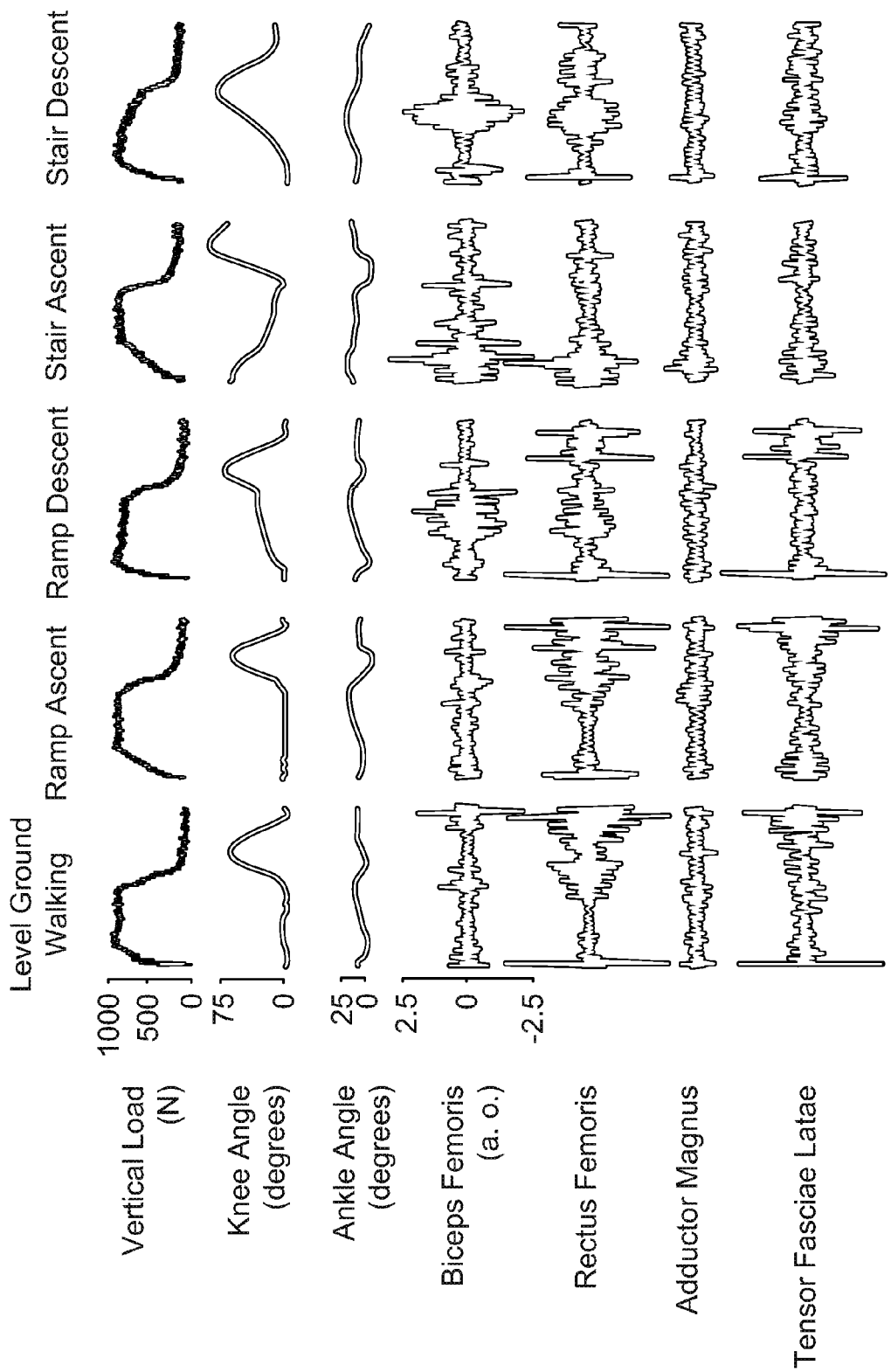
FIG. 6 is a representation of sample sensor data produced over the ambulation modes level walking, ramp ascent, ramp descent, stair ascent, and stair descent.

Testing data td from mechanical sensors 50 and electrodes 70 is collected during each ambulation mode and during the transitions between ambulation modes, and is saved in buffer 191 on microcontroller module 160. FIG. 6 displays sample testing data from certain sensors collected over the course of a gait cycle. Testing data td is collected throughout each gait cycle and is labeled with the ambulation mode in which the user was operating while testing data td was generated. In one embodiment, testing data td is saved in a file whose file name indicates the ambulation mode in which the user was operating. Alternately, testing data td may be saved in other formats that reflect the ambulation mode in which the user operated while testing data td was being generated.

Features in SFD 185s are generated by ambulation controller 400, which extracts features 415 from each gait cycle of training data td and stores them in SFD 186 along with the ambulation mode from which they were collected. Ambulation controller 400 additionally extracts features 415 from one or more instantaneous windows iw in each gait cycle of training data td, and stores those features and their labeled ambulation mode in IFD 185i. In one embodiment, ambulation controller 400 selects training data td from instantaneous windows iw prior to eight state points in a gait cycle: at 0%, 25%, 50%, and 75% of stance phase (where 0% of stance phase reflects heel strike of assistive device 10) and at 0%, 25%, 50%, and 75% of swing phase (where 0% of swing phase reflects toe-off of assistive device 10). Each instantaneous window iw is approximately 300 ms in duration. Ambulation controller 400 identifies the heel strike and toe off in each stride using data from mechanical sensors 50, such as from load cell 51, and calculates the remaining state points using heel strike and toe off information.

Upon instruction from the clinician, the ambulation controller 400 trains AMP 425 using feature database 185. In one embodiment, feature database 185 comprises tables for storing features 415 derived from data obtained from mechanical sensors 50 and electrodes 70. Features 415 for data from mechanical sensors 50 include the mean, minimum, maximum, and standard deviation. Features 415 for data from electrodes 70 include the mean absolute value, the number of zero crossings, the number of slope sign changes, the waveform length, and the first two coefficients of a sixth order autoregressive mode. Features other than features 415 that are known in the art could be used. Training of AMP 425 on the features in feature database 425 may be done with a button click to GUI 271, a press of a button on training remote 300, or another appropriate action.

AMP 425 is trained using feature database 185 using pattern recognition techniques known in the art. In one embodiment, AMP 425 is a pattern recognition controller employing a linear discriminant analysis ("LDA") method that is trained using cross validation. Once trained, AMP 425 takes an input vector of features 415 and returns a set of probabilities, with each probability reflecting the likelihood that the next stride of assistive device 10 will be in a particular ambulation mode.

In one embodiment, the controlled ambulation modes that are trained during the generalized training phase include level walking, ramp ascent, ramp descent, stair ascent, and stair descent. In another embodiment, the controlled ambulation modes that are trained include only level walking, stair ascent, and stair descent, which may provide for more accurate prediction results from AMP 425. In yet another embodiment, the controlled ambulation modes may include stumbling, obstacle avoidance, standing, turning, sit-to-stand, stand-to-sit, running, hopping, shuffling, or skipping.

New user training phase. Predictions from AMP 425 may be improved with respect to a new user (i.e. a user who did not participate in the generalized training phase) by further training AMP 425 with certain additional features added to feature database 185. In one embodiment, feature database 185 is updated using data d collected from a user operating assistive device 10 in level walking mode for approximately 20 minutes. As in the generalized training phase, features f are derived from the data d and added to IFD 185i. AMP 425 is then re-trained using IFD 185i. Retraining may occur with all features from IFD 185i. Alternately, retraining may occur with only those features from users whose physical characteristics (such as weight, height, or residual limb length) most closely resemble those of the new user (which subset would naturally include features f from the new user). The new user training described herein improves the prediction abilities of AMP 425 across all controlled ambulation modes with respect to the new user, even though the additional features f added to IFD 185i are derived only from level walking of the assistive device 10. The new user training phase reduces the training required for a new user and makes assistive device 10 more available to users who otherwise would not be able to complete the rigorous training, required by prior art systems, due to age or health difficulties.

Previous class estimator. After a user completes a stride (i.e. one completion of the gait cycle), embodiments of the system described herein may review data from mechanical sensors 50 and electrodes 70 collected during that stride to determine whether the ambulation mode of the stride had been predicted correctly by AMP 425. In one embodiment, AMP 425 uses information from prior strides to improve its prediction capabilities for future operation. On the first prediction—when no prior stride has been taken—the prior ambulation mode may be set to the starting ambulation mode of the assistive device 10 (such as "standing").

In one embodiment, AMP 425 may use ambulation mode probabilities from the prior state point (hereinafter known as "priors") in order to predict the current ambulation mode. In one embodiment, ambulation controller 400 comprises a prior stride recognizer 445, which uses the priors to determine the prior stride's actual ambulation mode, as follows. Prior stride recognizer uses a pattern recognition method, such as LDA, to compare features from the entire prior stride against SFD 185s. Prior stride recognizer 445 selects the most likely ambulation mode as the prior ambulation mode. If prior stride recognizer 445 determines that the most likely operation in the prior stride was a transition from one ambulation mode at the start of the stride to a different ambulation mode at the end of the stride, prior stride recognizer 445 selects the ambulation mode at the end of the stride as the prior ambulation mode.

Mode specific classers. For many ambulation modes, a limited number of transitions exist from that mode. As one example, a user who climbed stairs in the prior stride will either continue climbing stairs (if there are more stairs to climb) or transition to level walking (if all stairs have been climbed). After determining the ambulation mode of the prior stride, AMP 425 predicts the ambulation mode of the next stride. One embodiment of AMP 425 utilizes five mode-specific classifiers, each of which correspond to one of five controlled ambulation modes: level walking, stair ascent, stair descent, ramp ascent, and ramp descent. In one embodiment, only the following transitions are possible between ambulation modes during operation of assistive device 10: from level walking to one of level walking, stair ascent, stair descent, ramp ascent, or ramp descent; from stair ascent to one of stair ascent or level walking; from stair descent to one of stair descent or level walking; from ramp ascent to one of ramp ascent or level walking; and from ramp descent to one of ramp descent or level walking. For example, if the prior ambulation mode of assistive device 10 was stair ascent, AMP 425 uses features from the prior stride to determine whether those features indicate continued stair ascent or a transition to level walking. In another embodiment, the controlled ambulation modes are limited to level walking, stair ascent, and stair descent. With a smaller domain of controlled ambulation modes, error rates are further reduced.

Figure 7:
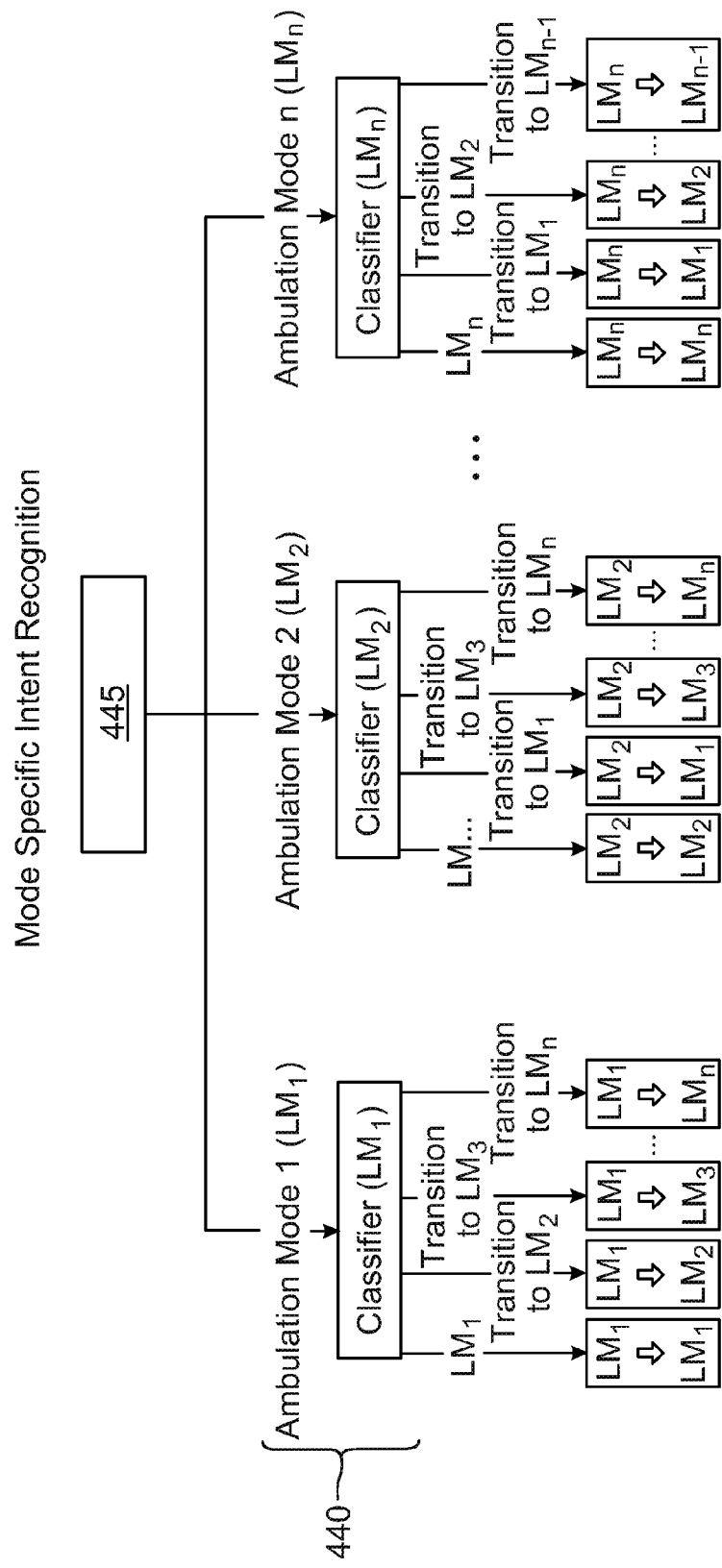
FIG. 7 is flow diagram of a mode specific intent recognition strategy implemented according to an embodiment of the invention.

FIG. 7 displays a generalized representation of one embodiment of AMP 425. As shown in FIG. 7, AMP 425 includes a series of ambulation mode classifiers 440, where each ambulation mode classifier 440i in the series 440 corresponds to an ambulation mode 440m. For each ambulation mode classifier 440i, AMP 425 also includes series of transition classes 441, where each transition class 441i in the series 441 corresponds to a possible transition from ambulation mode 440m to ambulation mode 441m. Each classifier 440i in the series of ambulation mode classifiers 440 is trained using a pattern recognition method, such as an LDA classifier, using features from IFD 185i that are labeled with transitions from ambulation mode 440m to any other ambulation mode (including ambulation mode 440m) corresponding to the series of transition classes 441. As shown in FIG. 7, prior stride recognizer 445 determines the prior ambulation mode. AMP 425 then selects an ambulation mode classifier amc from the series of ambulation mode classifiers 440 that corresponds to the prior ambulation mode. For example, if the prior ambulation mode is "level walking", AMP 425 selects the "level walking" classifier from series 440. Ambulation mode classifier amc then uses features 415 of the prior stride to predict the most likely transition mode, among possible transitions, from the prior ambulation mode. In one embodiment, features 415 of the prior stride are derived from an instantaneous window of approximately 300 ms prior to either heel strike or toe off. Table 1 lists sample values of feature data 415 derived from data collected in the instantaneous window prior to toe off. Table 2 lists sample values of feature data 415 derived from data collected in the instantaneous window prior to heel strike.

TABLE 1

Sample feature set derived from instantaneous window prior to toe-off.

| | Knee Angle | Load Cell | EMG Sensor |
| --- | --- | --- | --- |
| Mean | 3 | 1 | |
| Min | 0 | 0.3 | |
| Max | 5 | 1.05 | |
| Std Dev | 3 | 0.05 | |
| Mean Abs Val | | | 100 |
| Zero Crossings | | | 30 |
| Slope Sign Changes | | | 50 |
| Waveform Length | | | 200 |
| Autoregressive Feature 1 | | | 0.1 |
| Autoregressive Feature 2 | | | 0.05 |

TABLE 2

Sample feature set derived from instantaneous window prior to heel strike.

| | Knee Angle | Load Cell | EMG Sensor |
| --- | --- | --- | --- |
| Mean | 30 | 0.05 | |
| Min | 1 | 0 | |
| Max | 60 | 0.3 | |
| Std Dev | 20 | 0.05 | |
| Mean Abs Val | | | 100 |
| Zero Crossings | | | 2 |
| Slope Sign Changes | | | 5 |
| Waveform Length | | | 100 |
| Autoregressive Feature 1 | | | 0.003 |
| Autoregressive Feature 2 | | | 0.002 |

AMP 425 selects the most likely transition mode as the predicted ambulation mode, which is used by phase state controller 450 and torque controller 475 to control assistive device 10 to the predicted ambulation mode. In another embodiment, each ambulation mode classifier 440i further corresponds to a particular gait phase. Each classifier 440*i* is trained using features from IFD 185*i* that are labeled with ambulation mode transitions and the gait phase that corresponds to the classifier. In this embodiment, AMP 425 selects an ambulation mode classifier from the series of ambulation mode classifiers 440 that corresponds both to the prior ambulation mode as well as to the gait phase. AMP 425 may be used to predict the most likely ambulation mode of the next stride at multiple state points throughout the prior stride.

Time history information. In another embodiment of AMP 425, the AMP 425 utilizes features derived from instantaneous windows prior to a plurality of state points in order to improve the accuracy of ambulation mode prediction. Use data ud from mechanical sensors 50 and electrodes 70 are saved to microcontroller module 160 when assistive device 10 is in use. Ambulation controller 400 derives features from the use data ud over each gait cycle. Specifically, features are derived from use data ud generated during the same instantaneous windows used to generate features for IFD 185*i* in the generalized training phase (in one embodiment, the approximately 300 ms prior to each of 0%, 25%, 50%, and 75% of both stance and swing phase).

Figure 8:
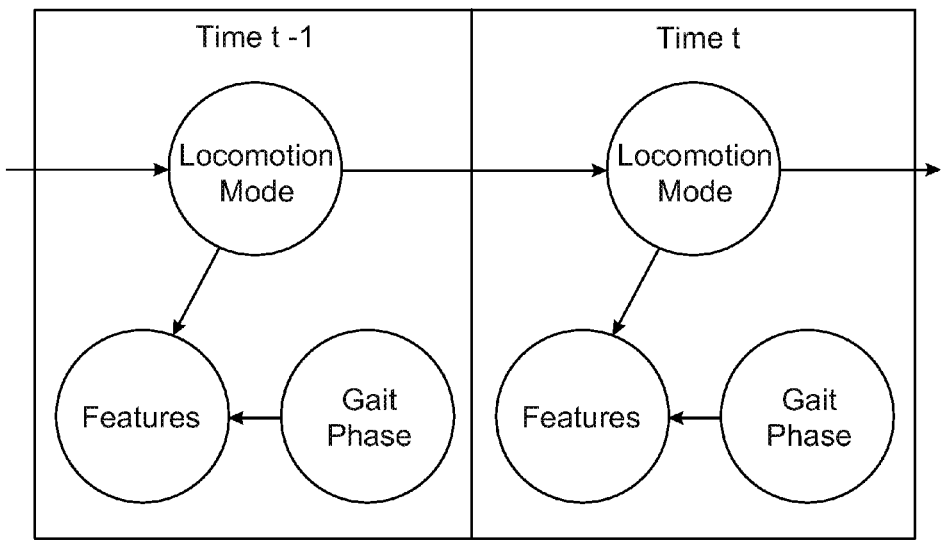
FIG. 8 displays a finite-state map of a Bayesian network that implements an embodiment of the time history strategy described herein.

At each state point, the ambulation controller 400 utilizes current feature and gait information to determine a set of probabilities, where each probability reflects the likelihood of an ambulation mode in the next stride. FIG. 8 shows a diagram of a two-time slice DBN graph. The arrows in FIG. 8 represent causality. Prior probabilities for each ambulation mode are propagated from time step to time step. Locomotion mode is the hidden unknown variable. The DBN fuses current likelihood information with the prior information through Bayes law which is given in equation 1 to form a maximum posterior probability (MAP) $p(C|\vec{x})$, which reflects the most likely ambulation mode of the next stride. In equation 1, $p(\vec{x}|C)$ is a vector containing the likelihood of each ambulation mode, given the features derived from the instantaneous window; $p(C)$ is the prior probability vector reflecting the prior set of ambulation mode probabilities, $p(\vec{x})$ is the observational probability, and $\hat{C}_{MAP}$ is the MAP estimate. In one embodiment, $p(\vec{x}|C)$ contains the probabilities predicted by one of the mode-specific classifiers described above.

$$\hat{C}_{MAP} = \mathrm{argmax}(p(C|\vec{x})) = \mathrm{argmax}\left(\frac{p(\vec{x}|C)p(C)}{p(\vec{x})}\right) \quad (1)$$

Between each step, the posterior probabilities of the prior step are transformed into the priors for the next step through a transitional probability matrix (φ or "TPM"). The TPM contains the probability of transitioning from one ambulation mode to another. The TPM is trained using the training data from the generalized training phase or can be set using values such as those shown in Table 3.

TABLE 3

Transitional probability matrix values.

| | | Probability of transition to class | | | | |
|---|---|---|---|---|---|---|
| | | Level walking | Ramp Ascent | Ramp Descent | Stair Ascent | Stair Descent |
| Probability of | Level walking | 0.92 | 0.02 | 0.02 | 0.02 | 0.02 |

TABLE 3-continued

Transitional probability matrix values.

| | | Probability of transition to class | | | | |
|---|---|---|---|---|---|---|
| | | Level walking | Ramp Ascent | Ramp Descent | Stair Ascent | Stair Descent |
| transition from class | Ramp Ascent | 0.2 | 0.8 | 0 | 0 | 0 |
| | Ramp Descent | 0.2 | 0 | 0.8 | 0 | 0 |
| | Stair Ascent | 0.2 | 0 | 0 | 0.8 | 0 |
| | Stair Descent | 0.2 | 0 | 0 | 0 | 0.8 |

In one embodiment, priors are updated using a TPM prepared using training data for each subject, where the TPM reflects the probability each transition occurred during the training data for that subject. Each subject may have a different transitional probability matrix. In addition to being generated from the training data in the TPM, priors can also be set manually or evolved using optimization algorithms such as a pattern search, simulated annealing or genetic algorithm. Equation 2 describes this transformation, where $(p(C|x)_{t-1})$ are the previous step's posterior probabilities and $p(C)_t$ are priors used at the current step.

$$P(C)_t = p(C|x)_{t-1} * \phi \quad (2)$$

The likelihood model was formed by assuming features to be a multivariate Gaussian function with equal class covariance (linear discriminant analysis (LDA) assumption). As with the mode specific class estimator, when no priors exist, the priors may be set to those for the starting mode of the assistive device 10 (such as "standing").

Table 4 displays sample probabilities calculated by AMP 425 across a prior stride in an example, where AMP 425 determines that assistive device 10 transitions from level walking to level walking at the end of stance phase. Over the course of the stride, ambulation controller 400 collects data from mechanical sensors 50 and electrodes 70. At the end of the stride, ambulation controller 400 calculates features 415 from the instantaneous windows prior to 25%, 50%, 75%, and 100% of stance phase. At 25% stance, AMP 425 uses the DBN to fuse prior probabilities with current probabilities determined by the mode specific methods described above, to result in a combined probability vector {0.95, 0.05, 0, 0, 0} as indicated in Table 4 below. AMP 425 multiplies the combined probability vector with the transitional probability matrix shown in Table 3 to calculate the priors for 50% stance. AMP 425 performs the same method at 50%, 75%, and 100% of stance, with the combined probability vector at 100% of stance {0.97, 0.03, 0, 0, 0} indicating that level walking is the most likely ambulation mode of the next gait phase.

TABLE 4

Exemplary time history probabilities during stance phase, indicating transition from level walking to level walking.

| | | Level Walking | Ramp Ascent | Ramp Descent | Stair Ascent | Stair Descent |
|---|---|---|---|---|---|---|
| 25% Stance | Prior | 0.4 | 0.2 | 0.2 | 0.1 | 0.1 |
| | Current | 0.9 | 0.1 | 0 | 0 | 0 |
| | Combined | 0.95 | 0.05 | 0 | 0 | 0 |

TABLE 4-continued

Exemplary time history probabilities during stance phase, indicating transition from level walking to level walking.

|  |  | Level Walking | Ramp Ascent | Ramp Descent | Stair Ascent | Stair Descent |
|---|---|---|---|---|---|---|
| 50% Stance | Prior | 0.88 | 0.06 | 0.02 | 0.02 | 0.02 |
|  | Current | 0.8 | 0.05 | 0.05 | 0.05 | 0.05 |
|  | Combined | 0.94 | 0.02 | 0.02 | 0.02 | 0.01 |
| 75% Stance | Prior | 0.88 | 0.04 | 0.04 | 0.02 | 0.02 |
|  | Current | 0.8 | 0.01 | 0.01 | 0.09 | 0.09 |
|  | Combined | 0.99 | 0.0005 | 0.0005 | 0.0035 | 0.0035 |
| 100% Stance | Prior | 0.91 | 0.02 | 0.02 | 0.02 | 0.02 |
|  | Current | 0.4 | 0.6 | 0 | 0 | 0 |
|  | Combined | 0.97 | 0.03 | 0 | 0 | 0 |

Table 5 displays sample probabilities calculated by AMP 425 across a prior stride in an example, where AMP 425 determines that assistive device 10 transitions from level walking to stair descent at the end of a swing phase.

TABLE 5

Exemplary time history probabilities during a swing phase, indicating transition from level walking to stair descent.

|  |  | Level Walking | Ramp Ascent | Ramp Descent | Stair Ascent | Stair Descent |
|---|---|---|---|---|---|---|
| 25% Stance | Prior | 0.9 | 0.05 | 0.02 | 0.02 | 0.02 |
|  | Current | 0.6 | 0.03 | 0.03 | 0.04 | 0.3 |
|  | Combined | 0.98 | 0.0025 | 0.0011 | 0.0014 | 0.0106 |
| 50% Stance | Prior | 0.9088 | 0.02 | 0.02 | 0.02 | 0.03 |
|  | Current | 0.01 | 0.01 | 0.01 | 0.07 | 0.9 |
|  | Combined | 0.25 | 0.0006 | 0.0057 | 0.04 | 0.7 |
| 75% Stance | Prior | 0.38 | 0.01 | 0.01 | 0.04 | 0.56 |
|  | Current | 0.01 | 0 | 0 | 0.3 | 0.69 |
|  | Combined | 0.01 | 0 | 0 | 0.03 | 0.96 |
| 100% Stance | Prior | 0.21 | 0.002 | 0.0002 | 0.022 | 0.7706 |
|  | Current | 0.49 | 0 | 0.01 | 0.01 | 0.49 |
|  | Combined | 0.21 | 0 | 0 | 0.0005 | 0.7881 |

Adaptive intent recognition. Another embodiment of AMP 425 uses adaptive intent recognition to further improve its ability to predict the present ambulation mode. After AMP 425 predicts the ambulation mode as described above, assistive device 10 attempts to operate in the predicted ambulation mode. The predicted ambulation mode, however, may differ from the ambulation mode in which the user of assistive deice 10 intends to operate. For instance, AMP 425 may predict that assistive device should transition to "stair ascent" mode, when in fact the user simply wishes to continue level walking. This error can cause assistive device 10 to kick or otherwise move improperly while the user is attempting to walk.

When a user operates assistive device 10, mechanical sensors 50 generate stereotypical gait profile data which, unlike EMG data, does not degenerate over time due to effects of continued use or user exhaustion. As described above, AMP 425 predicts the ambulation mode using a window of data taken prior certain state points WD. After predicting the ambulation mode, ambulation controller 400 causes assistive device 10 to operate in that ambulation mode. Ambulation controller 400 then records data from mechanical sensors 50 over a period of time, such as a gait cycle. At the end of the gait cycle, ambulation controller 400 compares features from the recorded data to features in feature database 185 to estimate the ambulation mode that assistive device 10 was in over the gait cycle. Comparison may be done using a pattern recognition technique such as LDA. Features from window data WD are then added to the feature database 185 with the label of the estimated ambulation mode. Adding features from window data WD in this fashion, with the label of the estimated ambulation mode, improves later ambulation mode predictions of the AMP 425 whether the estimated ambulation mode was the same as or different from the ambulation mode predicted on the basis of WD. If the predicted ambulation mode and the estimated ambulation mode are the same, then the AMP 425 correctly predicted the ambulation mode of the user and adding the additional features to feature database 185 retains AMP 425's predictive capabilities. If the estimated ambulation mode differs from the predicted ambulation mode, then the AMP 425 likely did not predict the correct estimation mode; however, adding the features from WD with the estimated ambulation mode label to feature database 185 improves, over time, AMP 425's predictive capabilities.

It should be understood that while use of the adaptive intent recognition is described above with respect to a full gait cycle, it could also be used more than once within a gait cycle. For instance, the adaptive intent recognition may take place at each toe-off as well as each heel-strike during use of assistive device 10.

It should be understood that in addition to controlling lower limb prostheses and orthoses, controller board 150 and its associated components may be used in analysis of able bodied movement with attachment of appropriate mechanical and EMG sensors. Such analysis could be useful, for instance, to monitor the falls of seniors or others in the home, or patients with conditions like Parkinson's disease. The systems and methods described herein could be used to determine why a patient fell, how the patient fell, to measure the outcomes of a patient's physical therapy, or to compare the effectiveness of different prostheses. Additionally, it should be understood that the systems and methods described herein could be implemented in other assistive devices such as trans-tibial, knee disarticulation, or other lower limb assistive devices.

Although the ambulation controller described above utilizes a specific set of features 415 and a specific set of state points (at 0%, 25%, 50%, and 75% of each of swing phase and stance phase), it should be understood that other values could be used. In one embodiment, ambulation controller 400 may identify state points on the basis of phase-based events. Such phase-based events may be determined by data from mechanical sensors 50. As an example, the zero crossing of data from knee velocity sensor 53, which represents a transition between flexion and extension of knee 20, may be a phase-based event used to identify a state point and its corresponding instantaneous window of data. Alternately, a state point may be identified using other phase variables, such as shank angle. Also, a different number of state points could be used, although a substantial decrease in the number of state points (such as a reduction to two state points, one in stance and one in swing) may increase transitional error. Finally it should be understood that alternative features could be stored in IFD 185 and SFD 186 and used to train AMP 425.

Phase state controller. Ambulation controller 400 implements impedance-based control of assistive device 10 through the use of finite state machines in phase state controller 450. In one embodiment, ambulation controller 400 divides each gait cycle of each ambulation mode into four phases: early-stance, late-stance, early swing, and late swing. A finite-state machine is used to transition between the four phases of each ambulation mode. The state-machine triggers are simple thresholds with logical AND/OR operators that interpret values from mechanical sensors 50. In one embodiment, early stance is triggered when the value of load cell 51 rises above a preset level 20% of a user's body weight; late stance is triggered when the ankle 30 angle crosses an eight degree angle; early swing is triggered when the load cell 51 value drops below a preset value of 30% of the user's body weight; and late swing is triggered when the velocity of the knee 20 crosses zero. These preset values may be adjusted by the clinician depending on each individual user's gait. For instance, the preset values may be adjusted upwards if the user tends to step hard while operating assistive device 10.

Figure 9:
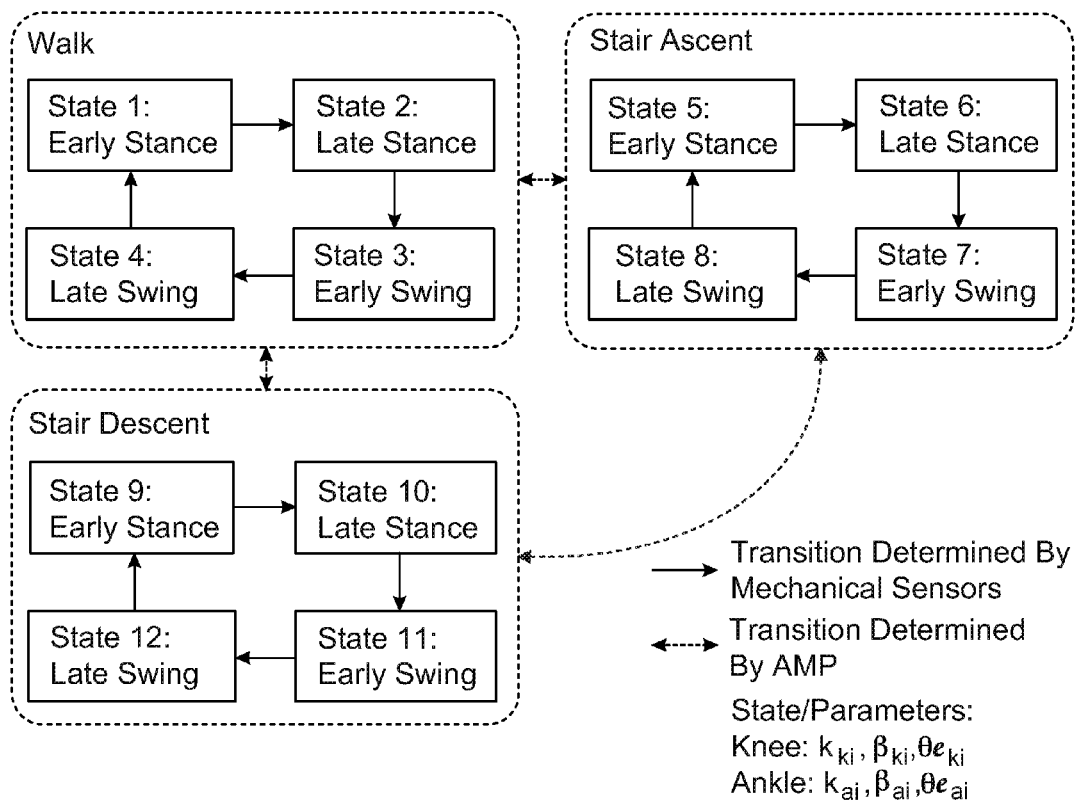
FIG. 9 represents possible finite state controllers in the walking, stair ascent, and stair descent ambulation modes, along with impedance parameters for each gait phase state.
Figure 10:
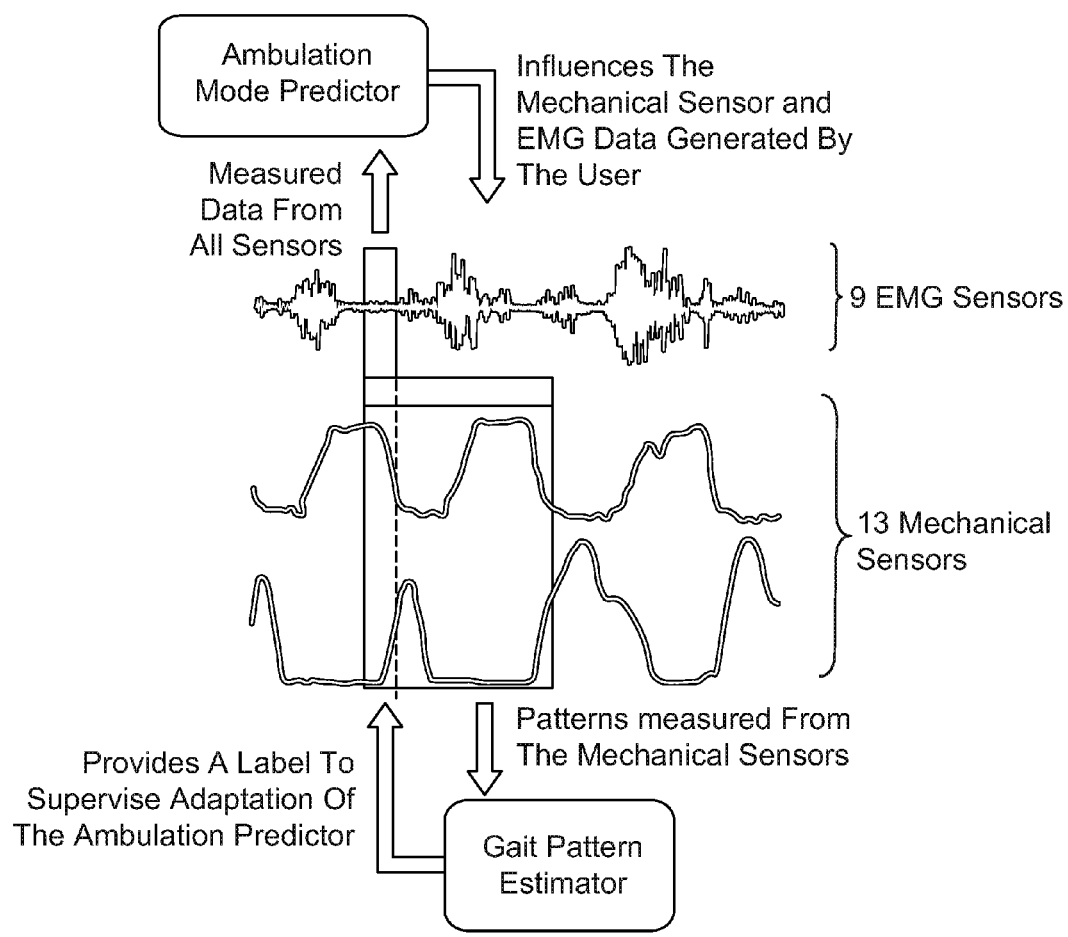
FIG. 10 displays a summary of one embodiment of the adaptive intent recognition method described herein.

FIG. 9 displays a representation of a finite state machine model for the ambulation modes level walking, stair ascent, and stair descent. Within each ambulation mode are the four phase states early stance, late stance, early swing, and late swing. The solid lines reflect transitions within the gait cycle, determined by mechanical sensors 50. For instance, when user operates assistive device 10 while walking, the phase state controller 450 causes assistive device 10 to start in the early stance phase state, and over the course of the stride transition to late stance, early swing, and then late swing. At the beginning of the next stride, assuming its ambulation mode remains walking, the phase state controller transitions the phase state of assistive device 10 back to early stance.

Within each phase state, phase state controller 450 assigns a set of values for impedance parameters 460 for each of the knee 20 and ankle 30. In one embodiment, impedance parameters 460 include stiffness, damping, and spring equilibrium angle. The impedance based architecture of phase state controller 450 may be implemented based on known strategies. Impedance parameters 460 adjust the stiffness of assistive device 10, where a higher stiffness holds the user up when assistive device 10 is in early stance or late stance and a low stiffness allows assistive device 10 to swing relatively freely when the user is in early swing or late swing. Values for impedance parameters 460 are initially set for a specific user by a clinician, using computer unit 250 or another appropriate method. After setting initial values for the impedance parameters 460 for each phase state of each ambulatory mode, the clinician may adjust the values after watching the user operate the assistive device 10 and on the basis of the user's perception of the stiffness during any phase state of any ambulation mode. For each joint of assistive device 10, impedance parameters 460 are included in phase state controller 450 for each gait phase of each ambulation mode. For instance, one set of values of impedance parameters 460 may include values for stiffness, damping, and spring equilibrium angle, for knee 20, for the "late stance" phase state of the "level walking" ambulation mode. Table 6 lists possible starting values for impedance parameters 460, where a positive theta knee value indicates knee flexion, a positive theta ankle value indicates plantar flexion, and the numbers after each mode reflect the gait phase (with "1" corresponding to early stance, "2" corresponding to late stance, "3" corresponding to early swing, and "4" corresponding to late swing).

TABLE 6

| | K Knee (NM/deg) | B Knee (NM/deg) | Theta Knee (deg) | K Ankle (NM/deg) | B Ankle (NM/deg) | Theta Ankle (deg) |
|---|---|---|---|---|---|---|
| Walk 1 | 3 | .25 | 0 | 7 | .25 | 0 |
| Walk 2 | 2 | ..05 | 10 | 7 | .25 | −12 |
| Walk 3 | .4 | .05 | 60 | 2.5 | .25 | 5 |

TABLE 6-continued

| | K Knee (NM/deg) | B Knee (NM/deg) | Theta Knee (deg) | K Ankle (NM/deg) | B Ankle (NM/deg) | Theta Ankle (deg) |
|---|---|---|---|---|---|---|
| Walk 4 | .5 | .08 | 0 | 2 | .15 | 0 |
| Ramp Up 1 | 3 | .25 | 0 | 7 | .25 | 0 |
| Ramp Up 2 | 2 | .05 | 10 | 9 | .2 | −12 |
| Ramp Up 3 | .4 | 0.05 | 50 | 2.5 | .25 | 0 |
| Ramp Up 4 | .5 | 0.08 | 0 | 2 | .15 | 0 |
| Ramp Down 1 | 2 | .25 | 0 | 5 | 0.25 | 0 |
| Ramp Down 2 | 1 | .1 | 30 | 5 | 0.1 | −5 |
| Ramp Down 3 | 1 | .05 | 50 | 2.5 | .2 | 0 |
| Ramp Down 4 | 0.5 | .08 | 0 | 2.5 | .15 | 0 |
| Stair Up 1 | 3 | .15 | 50 | 5 | .1 | 0 |
| Stair Up 2 | 3 | .15 | 0 | 5 | .1 | −15 |
| Stair Up 3 | 1 | 0.01 | 100 | 1.5 | .2 | 20 |
| Stair Up 4 | .5 | 0.1 | 50 | 1.5 | .2 | 15 |
| Stair Down 1 | 1.5 | .25 | 0 | 1.5 | .2 | −15 |
| Stair Down 2 | 1.5 | .25 | 30 | 1.5 | .2 | 0 |
| Stair Down 3 | 1 | .05 | 50 | 1.5 | .2 | 0 |
| Stair Down 4 | 0.45 | 0.1 | 0 | 1.5 | .2 | −15 |

It should be understood that alternate embodiments exist for phase state controller 450. Each ambulation mode could be divided into other phases than those described here, using other values from mechanical sensors 50. Phase state controller could utilize a different impedance based architecture, or even an architecture not based on impedance control. For instance, the phase state controller 450 method could be based on a determination of the center of pressure during stance phase.

Torque controller. Torque controller 475 uses phase state information from phase state controller 450 to control the motors that power assistive device 10. The torque controller 475 receives a phase state and values for impedance parameters 460 from phase state controller 450. Torque controller 475 then compares the phase state with the prior phase state of assistive device 10, and updates the phase state i to the new phase state if a transition has occurred. Torque controller next loads the values of impedance parameters 460 for the phase state i and computes the torque for the knee 20 and ankle 30 using the equations provided, where $\theta_k$ is the position value of knee 20 derived from position sensor 52, $\theta_a$ is the position value of ankle 30 derived from position sensor 54, $\dot{\theta}_k$ is the knee velocity derived from velocity sensor 53, $\dot{\theta}_a$ is the ankle velocity derived from velocity sensor 55, and k, e, and β represent impedance parameters 460 for the knee and ankle for state phase i. Finally, the torque values are sent to motors 41, which generate the intended torque to operate assistive device 10 in the predicted ambulation mode.

The invention claimed is:

1. A control unit comprising:
   a. a memory having stored thereon a feature database that includes feature data, a portion of which is labeled with a transition from an ambulation mode; and
   b. a memory having stored thereon a pattern recognition controller that is trained using the labeled feature data;
   wherein the pattern recognition controller is configured to predict the ambulation mode of an assistive device and the control unit is configured to naturally transition the assistive device from operating in a prior stride to operating in the predicted ambulation mode in a next stride, wherein the prior stride is the stride immediately prior to the next stride.

2. The control unit of claim 1:
a. wherein the feature database is further configured to be updated with features derived from data collected from said sensors during level walking of the assistive device; and
b. wherein the pattern recognition controller is further configured to be retrained on an updated feature database.

3. The control unit of claim 1:
a. wherein the pattern recognition controller comprises a classifier for each controlled ambulation mode.

4. The control unit of claim 1:
a. wherein the pattern recognition controller is configured to predict the next ambulation mode of the assistive device using features derived from the prior stride.

5. The control unit of claim 4:
a. wherein the pattern recognition controller is further configured to predict the ambulation mode of the assistive device using at least one of an LDA, a dynamic Bayesian network, a hidden Markov model, or a Kalman filter.

6. The control unit of claim 1:
a. wherein the feature database is configured to be updated with feature data derived from data collected from said sensors during the prior stride and labeled with a transition from an ambulation mode.

7. The control unit of claim 1:
a. wherein the control unit is configured to predict the ambulation mode of the assistive device using data collected from at least one electrode sensor coupled to the assistive device.

8. The control unit of claim 1, wherein the ambulation mode of the prior stride is a level walking mode and the ambulation mode of the next stride is a stair descent mode.

9. The control unit of claim 1, wherein the ambulation mode of the prior stride is a level walking mode and the ambulation mode of the next stride is a stair ascent mode.

10. The control unit of claim 1, wherein the ambulation mode of the prior stride is a level walking mode and the ambulation mode of the next stride is a ramp descent mode.

11. The control unit of claim 1, wherein the ambulation mode of the prior stride is a level walking mode and the ambulation mode of the next stride is a ramp ascent mode.

12. The control unit of claim 1, wherein the ambulation mode of the prior stride is a stair ascent mode and the ambulation mode of the next stride is a level walking mode.

13. The control unit of claim 1, wherein the ambulation mode of the prior stride is a stair descent mode and the ambulation mode of the next stride is a level walking mode.

14. The control unit of claim 1, wherein the ambulation mode of the prior stride is a ramp ascent mode and the ambulation mode of the next stride is a level walking mode.

15. The control unit of claim 1, wherein the ambulation mode of the prior stride is a ramp descent mode and the ambulation mode of the next stride is a level walking mode.

16. The control unit of claim 1, wherein the ambulation mode of the prior stride is the same as the ambulation mode of the next stride.

17. The control unit of claim 1, wherein the pattern recognition controller is configured to predict the ambulation mode of the next stride with an error rate equal to or less than three percent.

18. The control unit of claim 1, wherein the pattern recognition controller is configured to predict the ambulation mode of the next stride with an error rate equal to or less than two and a half percent.

19. The control unit of claim 1, wherein the pattern recognition controller is configured to predict the ambulation mode of the next stride with an error rate equal to or less than two and a two tenths of a percent.

20. The control unit of claim 1, wherein the feature data comprises the number of zero crossings in a signal collected from an electromyographic sensor.

21. The control unit of claim 1, wherein the feature data comprises the number of slope sign changes in a signal collected from an electromyographic sensor.

22. The control unit of claim 1, wherein the feature data comprises the waveform length of a signal collected from an electromyographic sensor.

23. The control unit of claim 1, wherein the assistive device is an artificial knee assistive device.

24. The control unit of claim 1, wherein the assistive device is an artificial knee prosthesis.

25. An assistive device comprising:
a. at least one powered joint;
b. a set of sensors coupled to the at least one powered joint;
c. a control unit, comprising a memory having thereon a pattern recognition controller, a feature database, and feature data contained in the feature database;
d. wherein the pattern recognition controller is configured to be trained on a portion of feature data that is labeled with a transition from an ambulation mode;
wherein the ambulation mode of the assistive device is configured to be predicted by the pattern recognition controller and wherein the assistive device is configured to provide a natural transition from operating in a prior stride to operating in the predicted ambulation mode in the next stride.

26. The assistive device of claim 25:
a. wherein the feature database is configured to be updated with features derived from data collected from said sensors during level walking of the assistive device; and
b. wherein the pattern recognition controller is configured to be retrained on an updated feature database.

27. The assistive device of claim 25:
a. wherein the pattern recognition controller comprises a classifier for each controlled ambulation mode.

28. The assistive device of claim 25:
a. wherein the pattern recognition controller is configured to predict the next ambulation mode of the assistive device using features derived from the prior stride.

29. The assistive device of claim 25:
a. wherein the feature database is configured to be updated with feature data derived from data collected from said sensors during the prior stride and labeled with a transition from an ambulation mode.

30. The assistive device of claim 25:
b. wherein the pattern recognition controller comprises a classifier for each controlled ambulation mode;
c. wherein the pattern recognition controller is configured to predict the next ambulation mode of the assistive device using features derived from the prior stride;
d. wherein the feature database is configured to be updated with feature data derived from data collected from said sensors during the prior stride and labeled with a transition from an ambulation mode;
e. wherein the feature database is configured to be updated with features derived from data collected from said sensors during level walking of the assistive device;
f wherein the pattern recognition controller is configured to be retrained on an updated feature database; and g. wherein the assistive device is configured to operate in the ambulation mode predicted by the pattern recognition controller.

31. The assistive device of claim 25, wherein the ambulation mode of the prior stride is a level walking mode and the ambulation mode of the next stride is a stair descent mode.

32. The assistive device of claim 25, wherein the ambulation mode of the prior stride is a level walking mode and the ambulation mode of the next stride is a stair ascent mode.

33. The assistive device of claim 25, wherein the ambulation mode of the prior stride is a level walking mode and the ambulation mode of the next stride is a ramp descent mode.

34. The assistive device of claim 25, wherein the ambulation mode of the prior stride is a level walking mode and the ambulation mode of the next stride is a ramp ascent mode.

35. The assistive device of claim 25, wherein the ambulation mode of the prior stride is a stair ascent mode and the ambulation mode of the next stride is a level walking mode.

36. The assistive device of claim 25, wherein the ambulation mode of the prior stride is a stair descent mode and the ambulation mode of the next stride is a level walking mode.

37. The assistive device of claim 25, wherein the ambulation mode of the prior stride is a ramp ascent mode and the ambulation mode of the next stride is a level walking mode.

38. The assistive device of claim 25, wherein the ambulation mode of the prior stride is a ramp descent mode and the ambulation mode of the next stride is a level walking mode.

39. The assistive device of claim 25, wherein the ambulation mode of the prior stride is the same as the ambulation mode of the next stride.

40. The assistive device of claim 25, wherein the pattern recognition controller is configured to predict the ambulation mode of the next stride with an error rate equal to or less than three percent.

41. The assistive device of claim 25, wherein the pattern recognition controller is configured to predict the ambulation mode of the next stride with an error rate equal to or less than two and a half percent.

42. The assistive device of claim 25, wherein the pattern recognition controller is configured to predict the ambulation mode of the next stride with an error rate equal to or less than two and a two tenths of a percent.

43. The assistive device of claim 25, wherein the feature data comprises the number of zero crossings in a signal collected from an electromyographic sensor.

44. The assistive device of claim 25, wherein the feature data comprises the number of slope sign changes in a signal collected from an electromyographic sensor.

45. The assistive device of claim 25, wherein the feature data comprises the waveform length of a signal collected from an electromyographic sensor.

46. The assistive device of claim 25, wherein the assistive device is an artificial knee assistive device.

47. The assistive device of claim 25, wherein the assistive device is an artificial knee prosthesis.

48. A method comprising:
   a. receiving a first data from at least one mechanical sensor coupled to the assistive device, the first data collected during a prior stride of the assistive device;
   b. receiving a second data from at least one electromyographic sensor coupled to the assistive device, the second data collected during the prior stride;
   c. predicting an ambulation mode of a next stride of the assistive device with a pattern recognition controller using feature values from the first data and the second data, wherein the pattern recognition controller has been trained on a database that includes feature data, a portion of which is labeled with a transition from an ambulation mode
   d. naturally transitioning the assistive device from the prior stride to the next stride; and
   e. operating the assistive device in the predicted ambulation mode during the next stride.

49. The method of claim 48, wherein the step of predicting an ambulation mode of the next stride comprises:
   a. determining the ambulation mode of the prior stride;
   b. selecting a classifier from a set of classifiers, each classifier in the set of classifiers being associated with an ambulation mode to which the assistive device may transition from the ambulation mode of the prior stride;
   c. predicting the ambulation mode of the next stride using the selected classifier.

50. The method of claim 49, wherein the step of predicting the ambulation mode of the next stride using the selected classifier comprises providing features derived from the first data and features derived from the second data to the selected classifier.

51. The method of claim 50, wherein the provided features are derived from a portion of the first data and a portion of the second data collected during one or more predetermined positions of the assistive device in the prior stride.

52. The method of claim 51, wherein the one or more predetermined positions comprises the position of the assistive device at about 25% of the prior stride.

53. The method of claim 51, wherein the one or more predetermined positions comprises the position of the assistive device at about 50% of the prior stride.

54. The method of claim 51, wherein the one or more predetermined positions comprises the position of the assistive device at about 75% of the prior stride.

55. The method of claim 51, wherein the one or more predetermined positions comprises the positions of the assistive device at about 25%, 50%, and 75% of the prior stride.

56. The method of claim 51, wherein the portion of the first data and the portion of the second data are collected during an approximately 300 ms period adjacent to each of the one or more predetermined positions.

57. The method of claim 48, further comprising providing a natural transition from the prior stride to the next stride, wherein the ambulation mode of the prior stride is a level walking mode and the ambulation mode of the next stride is a stair descent mode.

58. The method of claim 48, further comprising providing a natural transition from the prior stride to the next stride, wherein the ambulation mode of the prior stride is a level walking mode and the ambulation mode of the next stride is a stair ascent mode.

59. The method of claim 48, further comprising providing a natural transition from the prior stride to the next stride, wherein the ambulation mode of the prior stride is a level walking mode and the ambulation mode of the next stride is a ramp descent mode.

60. The method of claim 48, further comprising providing a natural transition from the prior stride to the next stride, wherein the ambulation mode of the prior stride is a level walking mode and the ambulation mode of the next stride is a ramp ascent mode.

61. The method of claim 48, further comprising providing a natural transition from the prior stride to the next stride, wherein the ambulation mode of the prior stride is a stair ascent mode and the ambulation mode of the next stride is a level walking mode.

62. The method of claim 48, further comprising providing a natural transition from the prior stride to the next stride, wherein the ambulation mode of the prior stride is a stair descent mode and the ambulation mode of the next stride is a level walking mode.

63. The method of claim 48, further comprising providing a natural transition from the prior stride to the next stride, wherein the ambulation mode of the prior stride is a ramp ascent mode and the ambulation mode of the next stride is a level walking mode.

64. The method of claim 48, further comprising providing a natural transition from the prior stride to the next stride, wherein the ambulation mode of the prior stride is a ramp descent mode and the ambulation mode of the next stride is a level walking mode.

65. The method of claim 48, further comprising providing a natural transition from the prior stride to the next stride, wherein the ambulation mode of the prior stride is the same as the ambulation mode of the next stride.

66. The method of claim 48, wherein the error rate of the predicting the ambulation mode of the next stride is equal to or less than three percent.

67. The method of claim 48, wherein the error rate of the predicting the ambulation mode of the next stride is equal to or less than two and a half percent.

68. The method of claim 48, wherein the error rate of the predicting the ambulation mode of the next stride is equal to or less than two and two tenths of a percent.

69. The method of claim 48, wherein the feature values comprise the number of zero crossings in a signal collected from an electromyographic sensor.

70. The method of claim 48, wherein the feature values comprise the number of slope sign changes in a signal collected from an electromyographic sensor.

71. The method of claim 48, wherein the feature values comprise the waveform length of a signal collected from an electromyographic sensor.

72. The method of claim 48, wherein the assistive device is an artificial knee assistive device.

73. The method of claim 48, wherein the assistive device is an artificial knee prosthesis.

* * * * *